United States Patent

Grollier et al.

Patent Number: 4,925,659
Date of Patent: May 15, 1990

[54] COSMETIC APPLICATION OF POLYSILOXANES CONTAINING A β-KETO ESTER GROUP AND COMPOSITIONS EMPLOYED

[75] Inventors: Jean F. Grollier, Paris; Claude Dubief, Le Chesnay, both of France

[73] Assignee: L'Oreal, Paris, France

[21] Appl. No.: 305,640

[22] Filed: Feb. 2, 1989

[30] Foreign Application Priority Data

Feb. 8, 1988 [LU] Luxembourg ............... 87127

[51] Int. Cl.$^5$ ............... A61K 31/74; A61K 7/06; A61K 7/00
[52] U.S. Cl. ............... 424/78; 424/70; 424/47; 424/DIG. 2; 424/DIG. 1; 524/265; 514/880; 514/881
[58] Field of Search ............... 424/70, 78, 47, DIG. 2, 424/DIG. 1; 524/265

[56] References Cited

U.S. PATENT DOCUMENTS

| | | | |
|---|---|---|---|
| 4,744,978 | 5/1988 | Homan et al. | 424/DIG. 2 |
| 4,808,649 | 2/1989 | Gay et al. | 524/268 |

FOREIGN PATENT DOCUMENTS

| | | |
|---|---|---|
| 3334208 | 9/1983 | Fed. Rep. of Germany. |
| 2602776 | 7/1988 | France. |

*Primary Examiner*—Joseph L. Schofer
*Assistant Examiner*—Carmen Pili-Curtis
*Attorney, Agent, or Firm*—Marshall, O'Toole, Gerstein, Murray & Bicknell

[57] ABSTRACT

Use in cosmetics of diorganopolysiloxanes containing a β-keto ester group, corresponding to the formula:

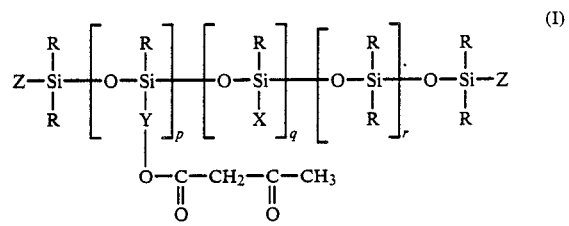

in which:

the groups R, which may be identical or different, denote, independently of one another, a $C_1$–$C_4$ alkyl, 3,3,3-trifluoropropyl, vinyl or phenyl groups, at least 80%, in numerical terms of the groups R being methyl radicals;

the groups Y, which may be identical or different, denote, independently of one another, a $C_1$–$C_{18}$ linear or branched alkylene link, optionally extended by a polyether chain;

the groups X, which may be identical or different, denote, independently of one another, a radical Y—OH or Y—OCOR′, Y having the meaning stated above and R′ being chosen from $C_1$–$C_{18}$ linear or branched alkyl or alkenyl groups;

the groups Z, which may be identical or different, denote, independently of one another, a group R as defined above or alternatively a radical

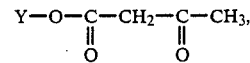

Y having the meaning stated above, it also being possible for Z to denote a group OR′ in which R′ has the meaning stated above;

p is an integer between 1 and 50 inclusive, and preferably between 1 and 16 inclusive;

q is an integer between 0 and 30 inclusive, and preferably between 0 and 8 inclusive; and r is an integer between 0 and 500 inclusive, and preferably between 2 and 50 inclusive;

or a mixture of these copolymers of formula (I), in which case p, q and r can be decimal numbers.

12 Claims, No Drawings

COSMETIC APPLICATION OF POLYSILOXANES CONTAINING A β-KETO ESTER GROUP AND COMPOSITIONS EMPLOYED

The present invention relates to the use in cosmetics of diorganopolysiloxanes containing a β-keto ester group, to the cosmetic compositions employed and also to the process for cosmetic treatment, especially of the hair and the skin.

Silicone oils are already used in cosmetics as a lubricant in compositions intended for the treatment and care of the hair and the skin. The oils in question are chiefly polydimethylsiloxanes.

Applicants has discovered, surprisingly, that the use of silicone oils consisting of diorganopolysiloxanes containing a β-keto ester group made it possible to obtain hair which was shiny and soft while having a non-greasy feel. These compounds also have the advantage of imparting softness and a non-sticky feel to the skin.

The term "cosmetic treatment" denotes a treatment aimed at obtaining on the hair one or more of the results stated above. The same applies to the cosmetic treatment of the skin.

A subject of the invention hence consists of the cosmetic use of diorganosiloxanes containing a β-keto ester group.

The subject of the invention is also a process for cosmetic treatment of the hair or the skin employing these compounds.

A further subject of the invention consists of the cosmetic compositions intended for the treatment of the skin or the hair, employing these compounds.

The diorganopolysiloxanes containing a β-keto ester group may be used as excipients in dermatological compositions for topical use containing an active substance.

Other subjects of the invention will become apparent on reading the description and the examples which follow.

The diorganopolysiloxanes containing a β-keto ester group used, according to the invention, in cosmetics are essentially characterized in that they correspond to the formula:

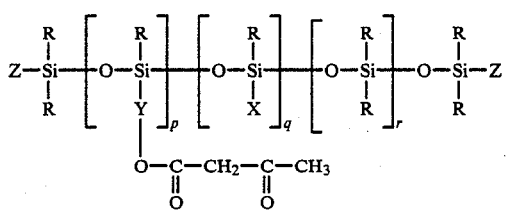

(I)

in which:

the groups R, which may be identical or different, denote, independently of one another, a $C_1$-$C_4$ alkyl, 3,3,3-trifluoropropyl, vinyl or phenyl group, at least 80%, in numerical terms, of the radicals R being methyl radicals, the groups Y, which may be identical or different, denote, independently of one another, a $C_1$-$C_{18}$ linear or branched alkylene link, optionally extended by a polyether chain chosen from polyethylene oxide and polypropylene oxide or mixtures thereof, the groups X, which may be identical or different, denote, independently of one another, a group Y—OH and Y—OCOR', Y having the meaning stated above and R' being chosen from $C_1$-$C_{18}$ linear or branched alkyl or alkenyl groups, the groups Z, which may be identical or different, denote, independently of one another, a radical R having the meaning stated above or alternatively a radical

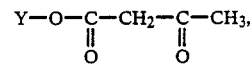

in which Y has the meaning stated above, it also being possible for Z to denote a group OR' in which R' has the meaning stated above, p is an integer between 1 and 50 inclusive, and preferably between 1 and 16 inclusive, q is an integer between 0 and 30 inclusive, and preferably between 0 and 8 inclusive, and r is an integer between 0 and 500 inclusive, preferably between 2 and 50 inclusive.

When the copolymers of formula (I) take the form of a mixture possessing the same units but differing in number, this mixture may be represented by an average formula (I) in which p, q and r can be decimal numbers.

Among especially preferred compounds used according to the invention, there may be mentioned the compounds of formula (I) in which:

R denotes an alkyl group chosen from methyl, ethyl, propyl and butyl groups, and the preferred diorganosiloxane units $R_2SiO$ are as follows:

$(CH_3)_2SiO$
$(CH_2=CH)(CH_3)SiO$
$(C_6H_5)(CH_3)SiO$
$(CF_3—CH_2—CH_2)(CH_3)SiO$

By way of a link Y, there may be mentioned:

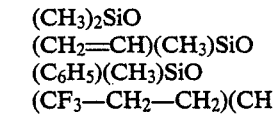

the group $—(CH_2)_3—$ is the preferred group for Y,

Z preferably denotes a radical R, and more especially a methyl group.

By way of a radical Y—OCOR', there may be mentioned:

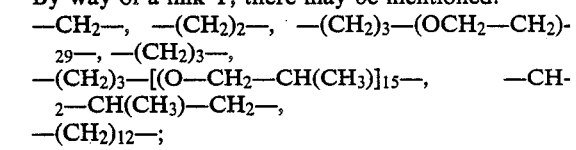

The radical R'COO preferably denotes an acrylate or methacrylate radical, that is to say R' is a $C_2$-$C_3$ (inclusive) alkenyl radical.

The copolymers of formula (I) can be statistical copolymers or block or sequence copolymers, according to the nature of the starting copolymers used for the synthesis of the copolymers of formula (I).

Especially preferred compounds are those in which R denotes a methyl group; Z denotes methyl and Y denotes a 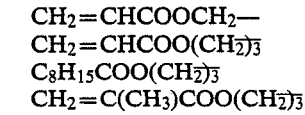 group; p is an integer or decimal number between 4.5 and 12; q is equal to 0 and r is an integer or decimal number between 6 and 45.

Diorganopolysiloxanes containing a β-keto ester group corresponding to the formula (I) may be prepared by reacting a suitable amount of diketene with a hydroxylated oil corresponding to the formula:

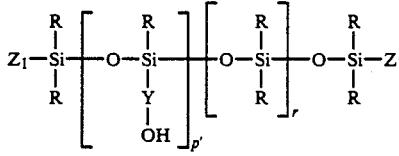

in which p'=p+q, R, Y and r have the meanings stated in relation to the formula (I) above and $Z_1$ denotes a group R or alternatively Y—OH.

This reaction can be optionally followed, in the case where q is other than zero, by esterification of the residual hydroxyl groups.

The reaction may be performed as a bulk reaction or preferably in an organic solvent medium such as ethyl acetate at atmospheric pressure, and preferably in the presence of an acid catalyst such as p-toluenesulphonic acid or basic catalyst such as a tertiary amine, for example trimethylamine or triethylamine.

The reaction of a diketene with a hydroxyalkyl group is known and has been described more especially by A. B. Boese, Industrial and Engineering Chemistry, Int. Ed. 32, 1940, pages 16 to 25, and by R. N. Lacey "Advances in Organic Chemistry Methods and Results", Vol. 2, pages 240 to 248.

In the case where it is desired to obtain a polymer of formula (I) in which q is equal to 0 and p'=p, a stoichiometric amount, or preferably an excess, of diketene is used, and this is removed at the end of the reaction, for example by distillation under reduced pressure.

In the case where it is desired to obtain a polymer of formula (I) in which q is other than 0, a suitable amount, less than the stoichiometric amount, of diketene is used, in accordance with the numbers p and q chosen beforehand.

The cosmetic compositions constituting one of the subjects of the invention are intended for the cosmetic care and treatment of the hair and the skin, and they contain, in a cosmetically acceptable medium, a diorganopolysiloxane containing a β-keto ester group corresponding to the formula (I) defined above, in concentrations preferably of between 0.5 and 50% by weight relative to the total weight of the composition, and especially between 1.5 and 30% by weight.

These compositions may be presented in various forms, such as aqueous dispersions and alcoholic or aqueous-alcoholic lotions, thickened or otherwise and optionally packaged as an aerosol.

They can contain, in addition to the diorganopolysiloxane of formula (I), adjuvants customarily used in cosmetics, such as perfumes, colourings, preservatives, thickeners, anionic, nonionic or amphoteric surfactants or mixtures thereof, sequestering agents, foam stabilizers, humectants and sunscreens, as well as substances which are active from the cosmetic or dermatological standpoint.

The cosmetic compositions, according to the invention, intended for the treatment of the hair, may be used, in particular, as shampoos, products to be rinsed for application before or after shampooing, before or after dyeing or bleaching or before or after permanent-waving or straightening, or as non-rinsed hair-styling products such as in setting or blow-drying lotions or alternatively in lacquers.

When the composition constitutes a shampoo, it contains, in a cosmetically acceptable medium, at least one or more anionic, nonionic or amphoteric surfactants or mixtures thereof; its total concentration of surfactants generally being between 0.5 and 30% by weight relative to the total weight of the composition, and preferably between 1.5 and 15% by weight.

When the compositions are used as products to be rinsed, these products may be presented in the form of lotions or aqueous dispersions, optionally thickened, or of gels.

The lotions can contain, in an aqueous medium, from 1 to 70% of a solvent which is cosmetically acceptable and more especially chosen from $C_1$–$C_4$ lower monohydric alcohols such as ethyl alcohol, n-propyl alcohol, isopropyl alcohol, tert-butyl alcohol; polyhydric alcohols such as ethylene glycol, diethylene glycol, propylene glycol; glycol ethers such as mono- or diethylene glycol alkyl ethers; and fatty acid esters such as isopropyl myristate.

When the compositions are thickened or are presented in the form of gels, they contain one or more thickeners which can be chosen from sodium alginate or gum arabic, cellulose derivatives such as methyl cellulose, hydroxymethyl cellulose, hydroxyethyl cellulose, hydroxypropyl cellulose, hydroxypropylmethyl cellulose and carboxymethyl cellulose, guar or its derivatives, heterobiopolysaccharides such as xanthan gum or scleroglucans and acrylic acid polymers, crosslinked or otherwise. It is also possible to obtain a thickening of the compositions by mixing polyethylene glycol and polyethylene glycol stearate or distearate or by a mixture of amides and phosphoric esters.

The composition may be thickened using the product resulting from ionic interaction of a cationic polymer comprising a copolymer of cellulose or of a cellulose derivative, grafted with a water-soluble quarternary ammonium monomer salt, and a carboxylic anionic polymer having an absolute capillary viscosity in dimethylformamide or methanol at a concentration of 5% and at 30° C. of not more than $30 \times 10^{-3}$ Pa.s, as described, more especially, in French patent application No. 2,598,611.

The thickeners are used in concentrations of between 0.1 and 30% by weight, and preferably between 0.2 and 15% by weight, relative to the total weight of the composition.

When the compositions intended for the treatment of the hair are used as non-rinsed hair-styling products, they contain, in an aqueous or solvent medium, the diorganopolysiloxanes of formula (I) optionally in the presence of thickening agents as defined above.

The solvents are preferably chosen from $C_2$–$C_4$ lower alcohols, and preferably consist of ethanol, and volatile silicones such as the cyclic silicones known in the CTFA dictionary by the names HEXAMETHYL-DISILOXANE and CYCLOMETHICONE, and mixtures thereof.

The solvents are used in proportions of between 5% and 99.5% by weight relative to the total weight of the composition.

The thickeners which are especially preferred in this case are chosen from acrylic acid polymers, crosslinked or otherwise, and more especially polyacrylic acids, crosslinked with a polyfunctional agent such as the products sold by the company Goodrich under the name Carbopol, cellulose derivatives such as are mentioned above, ethylene/maleic anhydride copolymers such as those sold by the company Monsanto under the name EMA 91 and copolymers of methyl vinyl ether and maleic anhydride such as those sold by the company GAF under the name Gantrez AN (119, 139, 169).

The concentration of thickening agents in these compositions varies between 0.05 and 5% by weight, and preferably between 0.1 and 2% by weight, relative to the total weight of the composition.

The compositions according to the invention may be packaged as an aerosol, to be distributed in the form of sprays and to form lacquers. In this case, the composition is used in the presence of a propellant gas such as, more especially, carbon dioxide, nitrogen, nitrous oxide, dimethylether, volatile hydrocarbons such as butane, isobutane and propane, and chlorinated and/or fluorinated hydrocarbons, and mixtures of hydrocarbons such as n-butane, isobutane and propane with chlorofluorohydrocarbons.

The cosmetic compositions intended for the treatment or care of the skin may be applied, in particular, in the form of bath or shower products, body oils, tanning products, shaving products, perfumed lotions, creams or milks.

These compositions contain, in a cosmetically acceptable medium, suitable for application on the skin and well known to those versed in the art, the diorganopolysiloxane derivatives of formula (I) defined above, in proportions which are also defined.

The cosmetic treatment process employing the diorganopolysiloxanes of formula (I) defined above consists essentially in applying the composition, either on the hair, according to the use envisaged (shampoo, treatment to be rinsed, hair-styling treatment without rinsing), or on the skin (bath, shower, and the like).

The examples which follow are designed to illustrate the invention without a limitation of the latter being implied.

The reference examples below are designed to illustrate the preparation of a number of compounds according to the invention, whereas the examples of compositions illustrate the cosmetic application of these compounds.

REFERENCE EXAMPLE 1

A 500-ml three-necked round-bottomed flask equipped with a central stirrer, a reflux condenser and a thermometer pocket, is charged with 100 g of a hydroxypropylated oil of average formula:

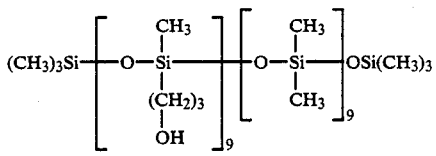

assaying at 468 meq/100 g with respect to the alcohol group. 1 ml of triethylamine as catalyst and 150 ml of a solvent, namely ethyl acetate, are added, and the homogeneous mixture thereby obtained is then heated to 45°–50° C. 41.5 g (0.494 mole) of diketene are introduced in the space of one hour, the temperature being maintained at 50° C. A slightly exothermal effect is noted, in particular at the beginning of the introduction. When the introduction is complete, the reaction mixture is left for a further hour at 50° C., and then allowed to return to room temperature. The excess diketene is removed by evaporation under reduced pressure (0.7 kPa) at 50°–60° C. A cloudy yellow oil is thereby obtained, which is filtered to obtain 138 g of a clear and odourless yellow oil.

By acidimetry using 0.5N aqueous sodium hydroxide in a water/acetone medium, the absence of strong acidity (dehydroacetic acid) is verified, and a weak acidity (of pKa approximately 10) of 331 meq/100 g and representing the β-keto ester group is titrated. The yield with respect to the β-keto ester group relative to the number of alcohol groups introduced is 97.6%.

The product obtained is represented by the following average formula:

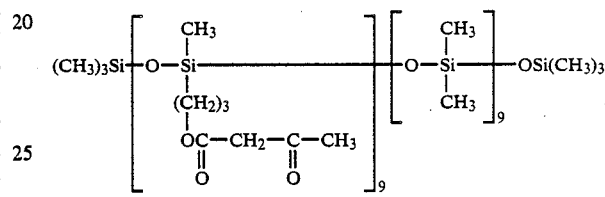

REFERENCE EXAMPLES 2 TO 6

By the same procedure as in Example 1, but modifying the composition of the initial gamma-hydroxypropylated oil, the products which follow, of average formula:

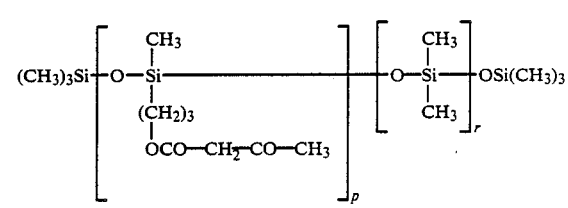

are prepared.

The values of p and r, as well as the titer t with respect to the β-keto ester group, expressed in meq/100 g, are collated in Table I below.

TABLE I

| Ex | p | r | t |
|---|---|---|---|
| 2 | 4.5 | 11 | 230 |
| 3 | 12 | 17 | 298 |
| 4 | 12 | 45 | 197 |
| 5 | 12 | 6 | 362 |
| 6 | 9 | 7.5 | 330 |

REFERENCE EXAMPLE 7

The procedure of Example 1 is repeated, starting with the same hydroxypropylated oil (100 g, 468 meq/100 g with respect to the alcohol group), except that a smaller amount of diketene is introduced (20 g, equivalent to 0.238 mole).

A clear and odourless yellow oil of average formula:

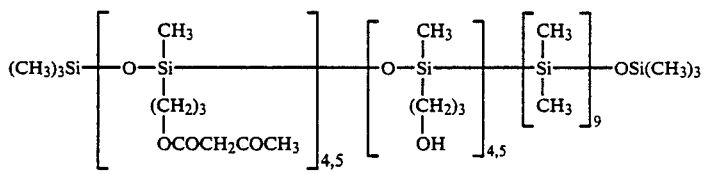

and possessing a titer with respect to the acetoacetate group of 188 meq/100 g, is obtained.

REFERENCE EXAMPLE 8

The starting substance is a gamma-hydroxypropylated oil of average formula:

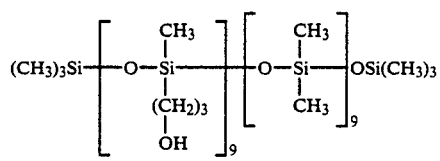

A partial esterification of the alcohol groups is performed on this oil with methyl methacrylate in the presence of dibutyltin oxide.

An oil of the following formula is obtained:

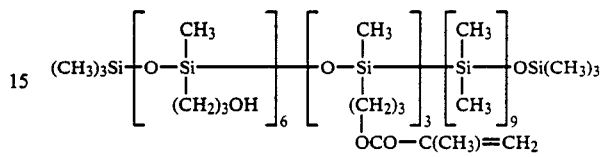

Diketene in slight excess is reacted, working as in Example 1. After removal of the excess diketene, a clear and odourless yellow oil of approximate formula:

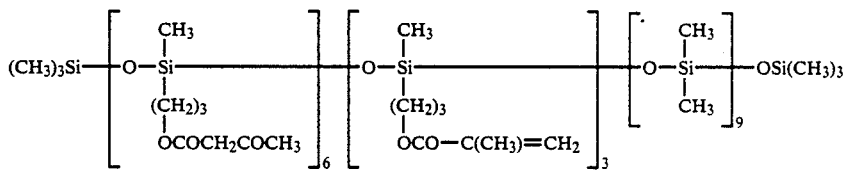

assaying at 220 meq/100 g with respect to the acetoacetate group, is obtained.

COMPOSITION EXAMPLE 1

A hair-styling gel to be rinsed, having the following composition, is prepared:

| | |
|---|---|
| Diorganopolysiloxane containing a β-keto ester group of formula: | 15 g |

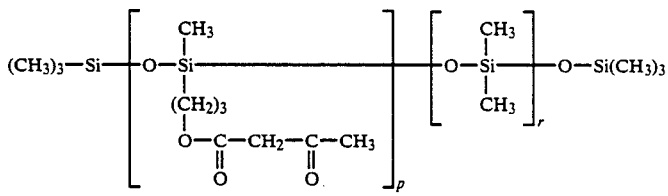

$p = 9 \quad r = 7.5$

| | |
|---|---|
| Titer with respect to the β-keto ester group in meq/100 g = 330 | |
| Crosslinked polyacrylic acid, MW = 4 million, sold under the name Carbopol 940 by the company Goodrich (neutralized with NH$_4$OH) | 1 g |
| Water qs | 100 g |

This gel is applied on washed and towel-dried hair. After rinsing, the hair is soft and the dried hair is shiny.

COMPOSITION EXAMPLE 2

A spray to be applied on dried hair, having the following composition, is prepared:

| | |
|---|---|
| Diorganopolysiloxane containing a β-keto ester group of formula: | 2 g |

-continued

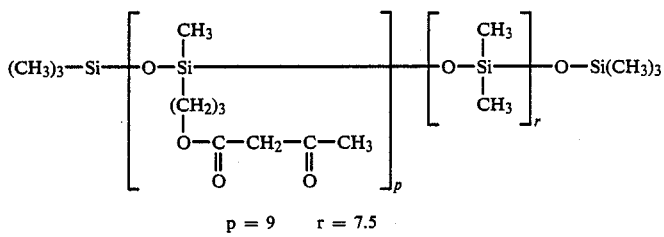

p = 9   r = 7.5

Titer with respect to the β-keto ester group in meq/100 g = 330
Absolute ethyl alcohol qs                                                                100 g This composition is packaged in a pump bottle. The spray imparts sheen to the hair without making it greasy.

COMPOSITION EXAMPLE 3

A hair-styling gel to be applied on dried hair, having the following composition, is prepared:

| | |
|---|---|
| Diorganopolysiloxane containing a β-keto ester group of formula: | 20 g |

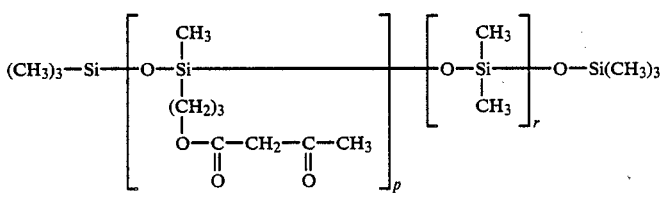

p = 9   r = 7.5

| | |
|---|---|
| Titer with respect to the β-keto ester group in meq/100 g = 330 | |
| Crosslinked polyacrylic acid, MW = 4 million, sold under the name Carbopol 940 by the company Goodrich (neutralized with NaOH) | 1 g |
| Perfume qs | |
| Water qs | 100 g |

After an application of the gel, the hair is soft and becomes shiny.

COMPOSITION EXAMPLE 4

A shower gel having the following composition is prepared:

| | |
|---|---|
| Oxyethylenated sodium alkyl (C$_{12}$–C$_{14}$) ether sulfate with 2,2 moles of ethylene oxide in aqueous solution at 25% AS | 10,0 g A.S. |
| Zwitterionic derivative compound of cocoa midopropyldimethylglycine at 30% AS in aqueous solution, sold under the name TEGO BETAINE HS by the Company GOLDSCHMIDT | 8,0 g A.S. |
| Isoparaffine sold under the name ISOPAR H by the Company EXXON CHEMICALS | 5,0 g |
| Diorganopolysiloxane containing a β-keto ester group of formula: | 1.0 g |

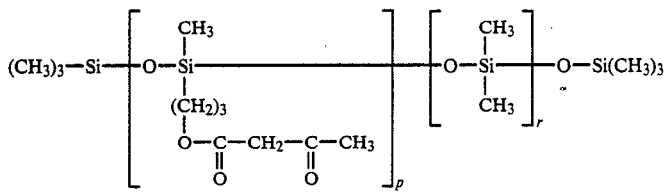

p = 9   r = 7.5

| | |
|---|---|
| Titer with respect to the β-keto ester group in meq/100 g = 330 | |
| Hcl qs pH = 5,5 | |
| waster qs | 100 g |

This shower gel, having a goof foaming power confers to the skin softness and a non-sticky feel.

COMPOSITION EXAMPLE 5

A softening cream for human body, having the following composition is prepared:

| | |
|---|---|
| Cetylic alcohol | 3,0 g |

| | |
|---|---|
| Mixture of cetylstearylic alcohol and oxiethylenated cetylstearylic alcohol with 33 moles of ethylene oxide, sold under the name SINNOWAX AO by the Company HENKEL | 2,0 g |
| diethyleneglycol stearate | 2,0 g |
| vaseline oil | 2,0 g |
| Xanthan gum sold under the name KELTRO T by the Company Kelco | 0,5 g |
| diorgano polysiloxane containing a β-keto ester group of formula: | 2,0 g |

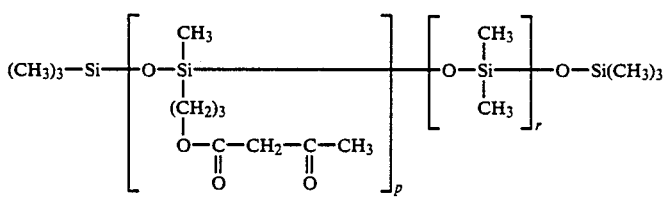

p = 9    r = 7.5

Titer with respect to the β-keto ester group in meq/100 g = 330
triethanolamine q.s. pH = 6
water q.s.                                                                                            100 g This cream is applied on the skin and confers softness and litheness.

We claim:

1. A cosmetic composition containing in a cosmetically acceptable medium water, at least one adjuvant chosen from solvents, perfumes, colorings, preservatives, thickeners, anionic, nonionic or amphoteric surfactants or mixtures thereof, sequestering agents, foam stabilizers, humectants, sunscreens, substances which are active in cosmetics and in dermatology and at least one diorganopolysiloxane containing a β-keto ester group, corresponding to the formula:

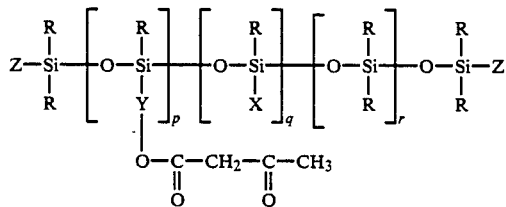

in which:
  the groups R, which may be identical or different, denote, independently of one another, C₁–C₄ alkyl, 3,3,3-trifluoropropyl, vinyl or phenyl groups, at least 80%, in numerical terms of the groups R being methyl radicals;
  the groups Y, which may be identical or different, denote, independently of one another, a C₁–C₁₈ linear or branched alkylene link, optionally extended by a polyether chain;
  the groups X, which may be identical or different, denote, independently of one another, a radical Y—OH or Y—OCOR', Y having the meaning stated above and R' being chosen from C₁–C₁₈ linear or branched alkyl or alkenyl groups;
  the group Z, which may be identical or different, denote, independently of one another, a group R as defined above or alternatively a radical

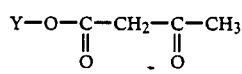

Y having the meaning stated above, it also being possible for Z to denote a group OR' in which R' has the meaning stated above;
  p is an integer between 1 and 50 inclusive, and preferably between 1 and 16 inclusive;
  q is an integer between 0 and 30 inclusive, and preferably between 0 and 8 inclusive; and
  r is an integer between 0 and 500 inclusive, and preferably between 2 and 50 inclusive;
  or a mixture of these copolymers of formula (I), in which case p, q and r can be decimal numbers.

2. A composition according to claim 1, wherein in the compound of formula (I), the groups R denotes a methyl, ethyl, propyl or butyl group; in that the diorganosiloxane groups of formula R₂SiO are chosen from:
  (CH₃)₂SiO
  (CH₂=CH)(CH₃)SiO
  (C₆H₅)(CH₃)SiO
  (CF₃—CH₂—CH₂)(CH₃)SiO
in that the links Y are chosen from:
  —CH₂—, —(CH₂)₂—, —(CH₂)₃—(OCH₂—CH₂)₂₉—, —(CH₂)₃—,
  —(CH₂)₃—[(O—CH₂—CH(CH₃)]₁₅—, —CH₂—CH(CH₃)—CH₂—,
  —(CH₂)₁₂—;
in that Z denotes a methyl radical;
in that the radical Y—OCOR' denotes a group chosen from:
  CH₂=CHCOOCH₂—
  CH₂=CHCOO(CH₂)₃
  C₈H₁₅COO(CH₂)₃
  CH₂=C(CH₃)COO(CH₂)₃
and in that the radical R'COO denotes an acrylate or methacrylate radical.

3. Composition for cosmetic treatment of the hair or the skin, containing, in a cosmetically acceptable medium, a diorganopolysiloxane containing a β-keto ester group of formula (I) as defined in claim 1, in concentrations of between 0.5 and 50% by weight relative to the total weight of the composition.

4. Composition according to claim 3, which is presented in the form of aqueous dispersions or alcoholic or aqueous-alcoholic lotions, thickened or otherwise, optionally packaged as an aerosol.

5. Composition according to claim 3, which is, intended for use as a shampoo, containing, in addition, at least one or more anionic, nonionic or amphoteric surfactants or mixtures thereof, in proportions of between 0.5 and 30% by weight relative to the total weight of the composition.

6. Composition according to claim 3, which is intended for use as a product to be rinsed, and is presented in the form of an aqueous dispersion, lotion, thickened lotion or gel.

7. Composition according to claim 6, containing at least 1 to 70% of solvent, chosen from lower alkanols, polyhydric alcohols, glycol ethers and fatty acid esters.

8. Composition according to claim 3, which is thickened or gelled with an agent chosen from sodium alginate, gum arabic, cellulose derivatives, guar gum, heterobiopolysaccharides, acrylic acid polymers, cross-linked or otherwise, a mixture of polyethylene glycol and polyethylene glycol stearate or distearate, a mixture of amide and phosphoric ester, and the product of ionic interaction between a cationic polymer comprising a copolymer of cellulose or a cellulose derivative, these being grafted with a water-soluble quarternary ammonium monomer salt, and a carboxylic anionic polymer having an absolute capillary viscosity in dimethylformamide or methanol at a concentration of 5% and at 30° C. of not more than $30 \times 10^{-3}$ Pa.s; this thickening agent is present in proportions of between 0.1 and 30% by weight relative to the total weight of the composition.

9. Composition according to claim 3, which is intended for use as a hair-styling product, without rinsing being employed, and containing in an aqueous or solvent medium, the diorganopolysiloxanes containing a $\beta$-keto ester group as defined in claim 1 or 2, the solvents being chosen from $C_2$-$C_4$ lower alkanols and volatile silicones.

10. Composition according to claim 9, containing thickeners chosen from acrylic acid polymers, cross-linked or otherwise, cellulose derivatives, ethylene/maleic anhydride copolymers and copolymers of methyl vinyl ether and maleic anhydride, in proportions of between 0.05 and 5% by weight.

11. Composition according to claim 3, which is packaged as an aerosol, to form a spray at the time of expulsion, in the presence of a propellant gas.

12. A composition for cosmetic treatment of the hair or skin according to claim 3 in the form of a bath or shower product, body oil, tanning product, shaving product, perfumed lotion, cream or milk.

* * * * *